United States Patent [19]

Furuya

[11] Patent Number: 4,978,617
[45] Date of Patent: Dec. 18, 1990

[54] PROCESS FOR PRODUCTION OF TOCOPHEROLS

[75] Inventor: Tsutomu Furuya, Tokyo, Japan

[73] Assignee: Showa Denko Kabushiki Kaisha, Tokyo, Japan

[21] Appl. No.: 690,906

[22] Filed: Jan. 14, 1985

[30] Foreign Application Priority Data

Jan. 13, 1984 [JP] Japan ................................ 59-3651

[51] Int. Cl.$^5$ .................. C12P 17/06; C12N 5/00; C12N 1/00
[52] U.S. Cl. .......................... 435/125; 435/240.48; 435/948
[58] Field of Search ............... 435/125, 240, 241, 317, 435/948, 240.48

[56] References Cited

PUBLICATIONS

Thomas et al. 1971. Quionones and α-Tocopherol in Greening Callus Cultures of Kalanchoëcrenata. New Phytol. 70:163–171.
Demir et al. 1979. The Fatty Acid Pattern and Tocapherol Content as Differential Characteristics... Chem Abstr. 90(25):#200333f.
Hagimori et al. 1978. Isolation and Identification of Abiquinone 9 from Cultured Cells of Safflower. Agric. Biol. Chem. 42(2):499–500.
Showa Denko K. K. 1985. Chem. Abstr. 102(1);#94352v (Abstract of Japanese Patent 154,998 Published 9/4/84).
Dyson, R. D. 1974. pp. 105,403 In: Cell Biology: A Molecular Approach, Allyn and Bacon, Inc., Boston.

*Primary Examiner*—Charles F. Warren
*Assistant Examiner*—David T. Fox
*Attorney, Agent, or Firm*—Sughrue, Mion, Zinn, Macpeak & Seas

[57] ABSTRACT

A new process for the production of tocopherols by tissue culture, which comprises (1) preparing a callus of a plant *Carthamus tinctorius*, (2) inoculating the callus into a synthetic nutrient medium and culturing the callus to produce tocopherols, and (3) recovering the tocopherols. The tocopherols thus produced are minaly α-tocopherol, which has the strongest vitamin E activity among tocopherol analogs.

3 Claims, No Drawings

PROCESS FOR PRODUCTION OF TOCOPHEROLS

BACKGROUND OF THE INVENTION

1. Field of the Invention

The present invention relates to a novel process for the production of tocopherols by the tissue culture of *Carthamus tinctorius*.

2. Description of the Related Art

Tocopherols occur naturally in many kinds of vegetable oils, and comprise analogs such as α-, β-, γ-, and δ-tocopherols, all having the same chroman structure. Although these analogs have different detailed actions and activity, all of them commonly have the physiological action of vitamin E and an antioxidant action. Thus, tocopherols are used as an ingredient of a pharmaceutical preparation and as an antioxidant for food. However, recently it has been found that tocopherols may have a physiological action such as bodily-condition deterioration-preventing or geriatric disease-preventing action, and accordingly, the demand for tocopherols obtained from vegetables is rapidly increasing.

Tocopherols are conventionally produced by a synthesis process or an extraction from vegetable origins. As described above, tocopherols occur in vegetable oils such as soy bean oil, wheat embryo oil, cotton seed oil, palm oil, corn oil, and the like. However, these vegetable oils generally have a low content of tocopherols. Therefore, tocopherols having a vegetable origin are usually obtained from scum formed in the deodorizing process of oil production, as this scum has a relatively high tocopherol content.

However, there are problems in the process for production of tocopherols from this scum; in that, since the scum is a by-product of an oil-production process, the amount of scum supplied depends on the amount of oil produced, and this amount rarely is enough to meet the increasing demand for tocopherols. This factor is the cause of many fluctuations in the cost of tocopherols. Further, although α-tocopherol is physiologically most effective, tocopherols produced from this scum contain analogs other than α-tocopherol, such as β-, γ-, and δ-tocopherols.

In view of the above problems, a new process for the production of tocopherols having a vegetable origin wherein α-analog-rich tocopherols are obtained in a large amount and at a low cost is strongly desired.

SUMMARY OF THE INVENTION

The present invention provides a new process for the production of tocopherols by tissue culture, which process comprises, (1) preparing callus from the plant *Carthamus tinctorius*, (2) inoculating the callus into a synthetic nutrient medium and culturing the callus to produce tocopherols, and (3) recovering the tocopherols.

DESCRIPTION OF THE PREFERRED EMBODIMENT

According to the present invention, first callus is prepared from the plant *Carthamus tinctorius*, which belongs to the Compositae and is an annual. To prepare the callus, the root, leaf, stem, embryo, shoot apex, bud, flower, seed, individual cells, or cultured cells or cultured tissue can be used as a starting material. In practice, however, the bud, seed or seedling, or cultured cells or differentiated cultured tissue are preferably used, since such starting materials contain tocopherols in relatively large amounts, can grow vigorously in a synthetic medium, and can be easily sterilized.

To prepare the callus, one of the above-described starting materials is inoculated into a synthetic nutrient medium which may be identical with a medium for the production of tocopherols described below in detail. The culture conditions for preparation of the callus may also be identical with those of the production culture described below in detail. The callus can be maintained substantially indefinitely by subculture of, for example, three weeks interval. For the subculture, the same culture medium and conditions as those of the callus preparation are used.

Then, to produce tocopherols, the callus is inoculated into a production medium.

According to the present invention, the medium used for the preparation and maintenance of the inoculum callus, and for the production of tocopherols, can be a conventional synthetic medium for plant tissue culture.

The above medium will contain a nitrogen source, carbon source, inorganic salts, vitamins, and plant growth regulators, and, optionally, growth stimulating substances and other organic substances. The nitrogen source is preferably a nitrate such as ammonium nitrate or potassium nitrate. The carbon source is preferably sucrose or glucose. The inorganic salts used include, for example, calcium chloride, magnesium sulfate, potassium diphosphate, ferrous sulfate, manganese sulfate, zinc sulfate, cobalt chloride, copper sulfate, sodium molybdate, potassium iodide, boric acid, and the sodium salt of EDTA, etc. The vitamins include, for example, nicotinic acid, nicotinic-acid amide, pyridoxine (hydrochloride), thiamine (hydrochloride), pantothenate, biotin, folic acid, Vitamin $B_{12}$, riboflavin, choline, and myo-inositol, etc. The plant growth regulators include auxins such as 2,4-dichlorophenoxyacetic acid, indolebutyric acid, indolebutyric acid, and naphthaleneacetic acid; cytokinins such as adenine, kinetin, benzyladenine, zeatin, and zeatin riboside; and gibberellin. The growth stimulating substances include, for example, yeast extract, malt extract, coconut milk, and casein-hydrolyzed product. The organic substances not mentioned above are, for example, amino acids such as glycine and glutamic acid.

The medium will contain some of the above-described materials. The representative media are, for example, Murashige & Skoog's medium, White's medium, Heller's medium, Linsmaier & Skoog's medium, Nitsch's medium, Gamborg's medium and modified media thereof, and so on. A modified Murashige & Skoog's medium (B2KC medium) described below in detail is preferable for the production of tocopherols.

Conventional conditions for plant tissue culture can be used for the culturing. The culture temperature is 15° C. to 35° C., preferably 20° C. to 30° C. The pH value of the medium is 4 to 8, preferably 5 to 6. The callus can be cultured on a solid medium or in a liquid medium under aerobic conditions. Suspension culture in a liquid medium is preferable. In the case of a liquid culture, the culture vessel is shaken, or aerated with mechanical stirring. The culturing may be carried out in the dark, or under the irradiation of a light having an appropriate wavelength and strength.

The culturing is continued until the amount of tocopherols produced reaches the maximum, for example, for 3 to 40 days, preferably 10 to 20 days.

Tocopherols produced in cultured cells may be recovered and purified according to a conventional method. For example, tocopherols are extracted from the cells by an appropriate solvent which can dissolve tocopherols, such as n-hexane, or a mixture of chloroform and methanol. The extract is then separated from the callus, and an aqueous phase, if present. Subsequently, tocopherols are separated from the solvent and purified according to a conventional method, such as adsorption chromatography, molecular distillation, and the like.

The present invention will now be illustrated by, but is by no means limited to, the following examples.

EXAMPLE 1

(1) Culturing

Buds of Carthamus tinctorius were sterilized by treatment with 70% ethanol for 5 minutes and a 10% solution of bleaching powder (insoluble portion removed by filtration) for 5 to 10 minutes. The outer covers were removed from the sterilized buds, and immature petals were obtained. The petals were cut into little pieces which were then washed with sterilized water. The washed pieces were then placed on the Murashige & Skoog's basal agar medium (abbreviated as DK medium) in a 100 ml Erlenmeyer flask for callus formation. The flask was then left in a dark environment at a temperature of 26° C. for three weeks. The pieces of petal callused at a rate of about 95%. The callus was maintained by subculture of three-week interval.

The composition of the DK medium is set forth in Table 1.

TABLE 1

Composition of DK medium (mg/l)

(inorganic component)

| | | | |
|---|---|---|---|
| $NH_4NO_3$ | 1650 | $KNO_3$ | 1900 |
| $CaCl_2.2H_2O$ | 440 | $MgSO_4.7H_2O$ | 370 |
| $KH_2PO_4$ | 170 | $FeSO_4.7H_2O$ | 27.8 |
| $Na_2$—EDTA | 37.3 | $MnSO_4.4H_2O$ | 22.3 |
| $ZnSO_4.4H_2O$ | 8.6 | $CoCl_2.6H_2O$ | 0.025 |
| $CuSO_4.5H_2O$ | 0.025 | $Na_2MoO_4.2H_2O$ | 0.25 |
| KI | 0.85 | $H_3BO_3$ | 6.2 |

(organic component)

| | | | |
|---|---|---|---|
| Nicotinic acid | 0.5 | Pyridoxine HCl | 0.5 |
| Thiamine HCl | 0.1 | myo-Inositol | 100 |
| Kinetin | 0.1 | | |
| 2,4-Dichlorophenoxyacetic acid | | | 1.0 |

The ingredients set forth in Table 1 were dissolved in purified water, and the solution was adjusted to pH 5.6 to 5.7 by adding 5% of potassium hydroxide solution, and then added with 3% sucrose, and optionally, 0.9% agar for a solid medium. 40 ml of the medium was then placed in a 100 ml Erlenmeyer flask.

A part of the callus maintained in the flask was removed and inoculated into a fresh PDK medium, and B2CK medium. The subculture for the callus on each medium was carried out at a three-week interval.

The PDK medium is the same as the DK medium but supplemented with 1 ppm of N-phenyl-N'-(4-pyridyl-)urea.

The B2KC medium is the same as the DK medium except that the organic components of the DK medium are replaced with the organic components set forth in Table 2.

TABLE 2

| Organic component of the B2KC medium (mg/l) | |
|---|---|
| Nicotinic-acid amide | 2.0 |
| Pyridoxine phosphate | 1.0 |
| Thiamine HCl | 1.0 |
| Calcium pantothenate | 1.0 |
| Biotin | 1.0 |
| Riboflavine | 0.5 |
| Folic acid | 0.5 |
| Choline HCl | 1.0 |
| Vitamin $B_{12}$ | 0.0015 |
| Inositol | 5,500 |
| Casamino acid | 1,000 |
| Indolebutyric acid | 2 |
| Kinetin | 0.1 |

The results of the tissue culture of Carthamus tinctorius carried out on the above-mentioned DK-, PDK-, and B2KC-solid (agar) medium by static culturing are set forth in Table 3.

TABLE 3

Growth of callus on the different solid media in static culture

| Medium | Amount of callus (g/flask) | | Growth ratio |
|---|---|---|---|
| | Inoculated | Harvested | |
| DK | 4.40 | 19.8 | 4.5 |
| B2KC | 4.51 | 78.9 | 17.5 |
| PDK | 3.77 | 33.2 | 8.8 |

(1)All values are an average of 10 flasks.

(2) Growth ratio is shown by $\frac{\text{amount of callus harvested}}{\text{amount of callus inoculated}}$.

(3)Culturing was carried out for three weeks in all cases.

In addition, a shaking culture was carried out for the B2KC- and DK-liquid media. The composition of the B2KC-liquid medium and the DK-liquid medium are identical with the B2KC-solid medium and the DK-solid medium, respectively, except that the liquid media do not contain agar.

The shaking culture was carried out by shaking the 500 ml or 1000 ml flasks, which contain 250 ml of the liquid medium and are inoculated with a piece of the callus, on a rotary shaker at 140 rpm or a reciprocating shaker at 80 spm. Other conditions were the same as for the static culture on the solid medium.

The result of the shaking culture is set forth in Table 4.

TABLE 4

Growth of callus in the different liquid media in shaking culture

| Medium | Amount of callus (g/flask) | | Growth ratio |
|---|---|---|---|
| | Inoculated | Harvested | |
| DK | | | |
| on rotary shaker | 14.3 | 82.9 | 5.8 |
| on reciprocating shaker | 15.0 | 43.5 | 2.9 |
| B2KC | | | |
| on rotary shaker | 13.5 | 101.3 | 7.5 |
| on reciprocating shaker | 11.8 | 94.4 | 8.0 |

(a)All values are an average of 4 flasks (b)Growth ratio has the same meaning as described in Table 3.

(c)Culturing was carried out for three weeks in all cases.

(2) Separation of tocopherol

The callus formed was filtrated, dried, and crushed. The resulting callus powder was extracted with n-hexane, and the extract separated from the residue by filtration. The filtrate was then subjected to a high performance liquid chromatography (HPLC). The conditions for the HPLC analysis were as follows:

Column: ZORBAX SIL (Shimadzu & Co.) $\phi$4.6 mm$\times$25 cm
Temperature: room temperature (about 25° C.)
Solvent: n-hexane/dioxane/ethanol (97.6:2.0:0.4)
Detection: fluorescense EX 289 nm, EM 325 nm
Flow rate: 1.5 ml/min.

The result is set forth in Table 5.

TABLE 5

| | | Amount of tocopherol | |
| | | Amount of tocopherol produced | |
| Medium | Culture condition | $\alpha$-tocopherol | $\beta$-tocopheral |
| | | (mg/100 g dired callus) | |
|---|---|---|---|
| DK | on rotary shaker | 1.0 | 0.3 |
| | on reciprocating shaker | 1.4 | 0.6 |
| B2KC | on rotary shaker | 5.6 | 1.3 |
| | on reciprocating shaker | 5.6 | 1.2 |

As seen from Table 5, the B2KC medium is preferable for the production of tocopherols, and most of the tocopherols produced in the callus of *Carthamus tinctorius* is $\alpha$-tocopherol, which is most effective among the tocopherol analogs as vitamin E. This means that, in practice, the present process is notably superior to the conventional processes.

I claim:

1. A process for the production of tocopherols by tissue culture, which comprises the steps of:
   (1) preparing a callus of a plant *Carthamus tinctorius*,
   (2) inoculating the callus into a synthetic nutrient medium and culturing the callus to produce tocopherols, and
   (3) recovering the tocopherols.

2. A process according to claim 1 wherein the callus is prepared from a member selected from the group consisting of the root, leaf, stem, embryo, shoot apex, bud, flower, seed, individual cells, cultured cells and cultured tissue.

3. A process according to claim 1 wherein the produced tocopherols are mainly $\alpha$-tocopherol.

* * * * *